United States Patent [19]

Ballentine

[11] Patent Number: 4,679,423
[45] Date of Patent: Jul. 14, 1987

[54] METHOD AND APPARATUS FOR MEASURING THE PORE SIZE OF ENHANCED TUBES

[75] Inventor: Paul H. Ballentine, Cazenovia, N.Y.

[73] Assignee: Carrier Corporation, Syracuse, N.Y.

[21] Appl. No.: 809,619

[22] Filed: Dec. 16, 1985

[51] Int. Cl.⁴ ............................................. G01B 13/08
[52] U.S. Cl. ..................................................... 73/37.5
[58] Field of Search ........................ 73/37.5, 37.8, 37.9

[56] References Cited

U.S. PATENT DOCUMENTS

| | | | |
|---|---|---|---|
| 3,508,432 | 4/1970 | Marshall, Jr. et al. | 73/37.8 |
| 3,728,894 | 4/1973 | Stern | 73/37.5 |
| 4,001,359 | 1/1977 | Fisher et al. | 73/37.5 |
| 4,088,009 | 5/1978 | Fukuda | 73/37.8 |
| 4,510,805 | 4/1985 | Saint-Amour | 73/37.9 |
| 4,550,592 | 11/1985 | Dechape | 73/37.5 |

FOREIGN PATENT DOCUMENTS 119357  4/1958  U.S.S.R. ................. 73/37.5

Primary Examiner—Stewart J. Levy
Assistant Examiner—Hezron E. Williams
Attorney, Agent, or Firm—Robert H. Kelly

[57] ABSTRACT

A method and apparatus for measuring the pore size on the surface of an externally enhanced evaporator tube. The apparatus is the pneumatic equivalent of an electrical wheatstone bridge circuit. Air is fed into two parallel legs of a circuit. The first leg has a variable flow control valve in series with a reference fixture having a fixed orifice therein. The other leg has a variable flow control valve in series with a test fixture matingly engaged with the enhanced tube to be measured. A differential pressure transducer measures the difference between the air pressure drop across the enhanced tube and the air pressure drop across the reference orifice plate. Therefore, any changes in the pressure, temperature, or humidity of the supply air will affect both legs in the same manner, so the reading of the transducer will not be affected by changes in supply air.

3 Claims, 5 Drawing Figures

METHOD AND APPARATUS FOR MEASURING THE PORE SIZE OF ENHANCED TUBES

BACKGROUND OF THE INVENTION

This invention relates generally to the manufacture of enhanced tubes and more particularly to a method of and an apparatus for measuring the pore size in an externally enhanced evaporator tube.

In an evaporator of certain refrigeration systems a fluid to be cooled is passed through heat transfer tubing while refrigerant in contact with the exterior of the tubing changes state from a liquid to a vapor by absorbing heat from the fluid within the tubing. The external and internal configuration of the tubing are important in determining the overall heat transfer characteristics of the tubing. For example, it is known that one of the most effective ways of transferring heat from the fluid within the tube to the boiling refrigerant surrounding the tube is through the mechanism of nucleate boiling.

It has been theorized that the provision of vapor entrapment sites or cavities on a heat transfer surface cause nucleate boiling. According to this theory the vapor trapped in the cavities forms the nucleus of a bubble, at or slightly above the saturation temperature, and the bubble increases in volume as heat is added until surface tension is overcome and a vapor bubble breaks free from the heat transfer surface. As the vapor bubble leaves the heat transfer surface, liquid enters the vacated volume trapping the remaining vapor and another bubble is formed. The continual bubble formation together with the convection effect of the bubbles traveling through and mixing the boundary layer of superheated refrigerant, which covers the vapor entrapment sites, results in improved heat transfer. A heat exchange surface having a number of discrete artificial nucleation sites is disclosed in U.S. Pat. No. 3,301,314.

It is known that a vapor entrapment site or cavity produces stable bubble columns when it is of the re-entrant type. In this context, a re-entrant vapor entrapment site is defined as a cavity or groove in which the size of the surface pore or gap is smaller than the subsurface cavity or subsurface groove. Heat transfer tubes having re-entrant type grooves are disclosed in U.S. Pat. Nos. 3,696,861 and 3,768,290.

It has been discovered that an excessive influx of liquid from the surroundings can flood or deactivate a re-entrant type vapor entrapment site. However, a heat transfer surface having subsurface channels communicating with the surroundings through surface openings or pores having a specified "opening ratio" have been found to provide good heat transfer and prevent flooding of the vapor entrapment site or subsurface channel.

In regard to the interior surface configuration of a heat transfer tube, it is known that providing an internal rib on the tube may enhance the heat transfer characteristics of the tube due to the increased turbulence of the fluid flowing through the ribbed tube.

As disclosed in U.S. Pat. Nos. 4,425,696 and 4,438,807 assigned to the present assignee and incorporated by reference herein, an internally and externally enhanced heat transfer tube, having an internal rib and an external helical fin (creating a subsurface channel) communicating with the surrounding liquid through surface openings (pores) is manufactured by a single pass process with a tube finning and rolling machine. According to the disclosed process a grooved mandrel is placed inside an unformed tube and a tool arbor having a tool gang thereon is rolled over the external surface of the tube. The unformed tube is pressed against the mandrel to form at least one internal rib on the internal surface of the tube. Simultaneously, at least one external fin convolution is formed on the external surface of the tube by finning discs on the tool gang. The external fin convolutions form subsurface channels therebetween. The external fin convolutions also have depressed sections above the internal rib where the tube is forced into the grooves of the mandrel to form the rib. A smooth roller-like disc on the tool arbor is rolled over the external surface of the tube after the external fin convolution is formed. The smooth roller-like disc is designed to bend over the tip portion of the external fin so that it touches the adjacent fin convolution and forms an enclosed subsurface channel. However, the tip portion of the depressed sections of the external fin, which are located above the internal rib, are also bent over but do not touch the adjacent convolutions, thereby forming pores which provide fluid communication between the fluid surrounding the tube and the subsurface channels.

The performance of the foregoing tube is critically dependent upon the external enhancement of the tube. It is therefore important to maintain a consistent subsurface channel size and pore size during the manufacturing process. Normal variations in subsurface channel size and surface pore size do occur, however, due to tool wear, material variations in the tube, dimensional variations in the tube lengths, and machine tolerances. In order to account for these variables and to maintain a consistent pore size, it is necessary to measure the pore size on each tube produced and adjust the finning machine to maintain the correct subsurface channel and pore sizes. However, the prior methods of checking the pore size in an enhanced tube were very laborious and expensive processes, and could not be used in a manufacturing process. For example, one method was to have an operator randomly select a manufactured tube and optically check the pore size of the selected tube under a microscope. Another method was to take a photograph of a tube and using an image analyzer compare the area of the pores in a selected area to the area of the pores in a reference photograph. However, these methods were time consuming and did not provide the quality and quantity of tubes necessary for a manufacturing process.

Thus, there was a clear need for a method and apparatus for measuring the size of the surface pores in an enhanced tube that would, to a large extent, overcome the inadequacies that have characterized the prior art.

SUMMARY OF THE INVENTION

A pneumatic pressure device for measuring the pore size on the surface of an enhanced evaporator tube has been developed. This measuring device is characterized by a sealed chamber in contact with the enhanced tube surface, whereby compressed air flows into the chamber and into the pores on the surface of the enhanced tube and through the subsurface channels in the tube and out a pore to the surrounding environment. The pressure drop across the surface pores on the tube relates to the size of the subsurface channels and pores, and thus correlates to the expected boiling heat transfer coefficient of the tube. The instrument used to measure the pressure in the chamber is adversely effected by changes in system air temperature, the humidity in the air system, and fluctuations in the supply pressure.

However, in the present invention an orifice plate having a known resistance to air flow is provided in one leg of a measuring system, and the enhanced tube to be measured is used in the other leg of the system to provide the pressure inputs to a differential pressure transducer.

Accordingly, it is an object of the present invention to provide a system which measures the average pore size on an enhanced tube surface.

Another object of the present invention is to provide a measurement system which can inspect 100% of the enhanced tubes that are produced.

A further object of the present invention is to provide a measurement system which compensates for changes in temperature, humidity, and pressure of the supply air.

These and other objects of the present invention are attained by a novel apparatus and method for measuring the pore size on an enhanced evaporator tube. The measurement system comprises a regulated air supply connected in parallel to a fixed reference orifice plate and the enhanced tube to be measured whereby the differences between the air pressure drops across the enhanced tube and the air pressure drop across the reference orifice plate is measured by a differential pressure transmitter and corresponds to the size of the pores in the enhanced tube. Thus, the present invention measures the average pore size of an enhanced tube and compensates for any changes in the pressure, temperature, or humidity of the supply air.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

Other objects and advantages of the present invention will be apparent from the following detailed description in conjunction with the accompanying drawings, forming a part of this specification, and in which reference numerals shown in the drawings designate like or corresponding parts throughout the same, in which.

DESCRIPTION OF THE PREFERRED EMBODIMENT

The embodiment of the present invention described below is especially designed for use with enhanced evaporator tubes because these tubes have a critical dimension which must be precisely controlled in order to maintain good heat transfer performance. These enhanced tubes are designed for use in an evaporator of a refrigeration system having a fluid to be cooled passing through the tubes and having refrigerant, which is to be vaporized, in contact with the external surfaces of the tubes. Typically, a plurality of heat transfer tubes are mounted in parallel and connected so that several tubes form a fluid flow circuit and a plurality of such parallel circuits are provided to form a tube bundle. Usually, all of the tubes of the various circuits are contained within a single shell wherein they are immersed in the refrigerant. The heat transfer capability of the evaporator is largely determined by the average heat transfer characteristics of the individual heat transfer tubes. The heat transfer characteristics of an individual tube is, in turn, influenced by the size of the subsurface channels and pores on the surface of the tubes are critical. Therefore, it is important to maintain a consistent subsurface channel size and pore size during the manufacturing process of the enhanced evaporator tube.

Figure 1:
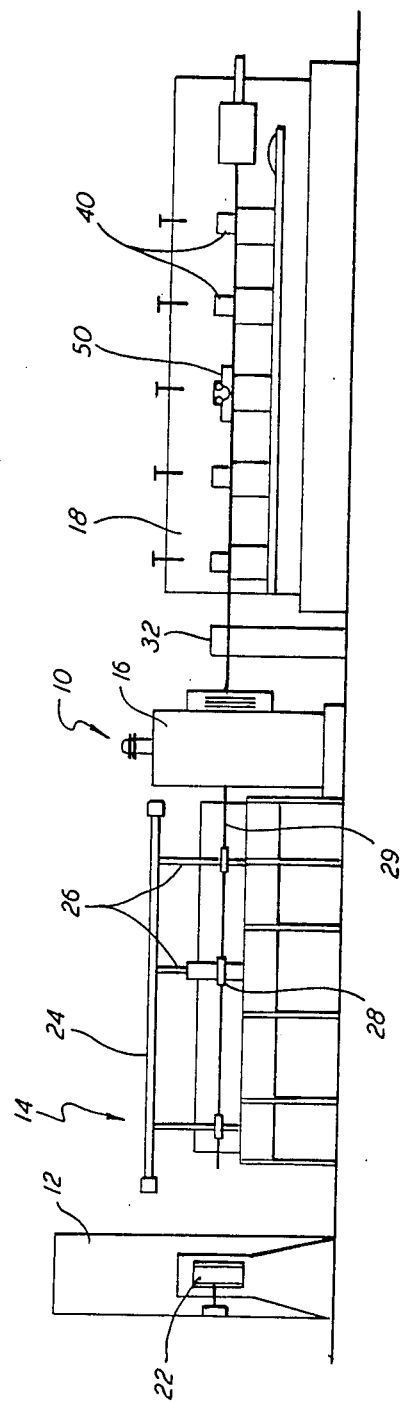
FIG. 1 is a schematic representation of a finning machine for the manufacture of enhanced tubes and the measurement of the pore size of the enhanced tubes in accordance with the present invention.

Referring now to the drawings, FIG. 1 is a diagrammatic representation of a finning station for manufacturing enhanced tubes in accordance with the principles of the present invention. The finning station 10 includes an electronic control cabinet 12, a feed section 14, a finning head section 16, an ejection section 32, and a pore measurement section 18. The electronic control cabinet includes a programmable controller and an operator console 22. The programmable controller performs logic execution, timing, sequencing, and calculations for the finning operation. The feed section 14 generally includes two similar parallel mandrels 24 (the two mandrels are generally in the same horizontal plane, thus, the rearward mandrel is not shown in the Figure) typically supported by a plurality of support arms 26 and positioned by piston means 28. Accordingly, the operator will load a blank tube on the front and rear mandrels 24 and cycle the feed section 14 such that one mandrel, e.g. the front mandrel, will drop down and move the blank tube along the longitudinal finning axis 29 into the finning head section 16. When the blank tube is completely enhanced the mandrel will retract to its original position while ejection means, e.g. eject wheels, in the ejection section 32, will engage the enhanced tube and send it into the pore measurement section 18. Once the enhanced tube is completely into the pore measurement section 18 and the front mandrel is in its original position, the rear mandrel will drop down and the process will repeat itself. Moreover, the enhanced tube in the cavity measurement section 18 is matingly engaged by measuring apparatus 40 for measuring the pore size on the surface of the evaporator tube. A fixed reference orifice means 50 provides a reference pressure drop.

Figure 2:
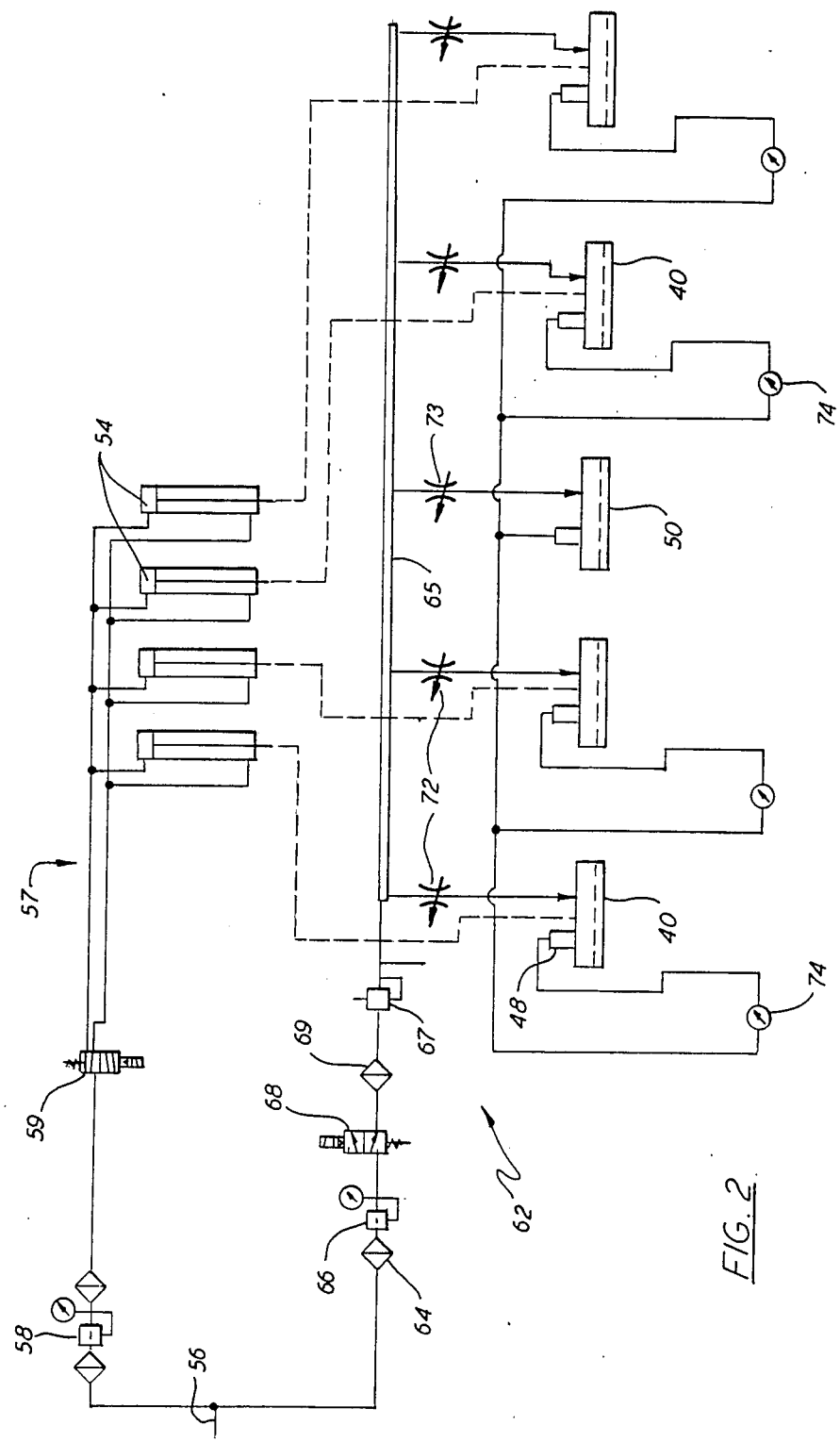
FIG. 2 is a pneumatic schematic representation of the enhanced tube measuring device in accordance with the present invention.

Referring now to FIG. 2, a pneumatic schematic of the enhanced tube measuring device is shown. The pore measurement section 18 is comprised of two separate pneumatic circuits, 57 to actuate the clamping mechanisms 54, and 62 to supply the air for the measuring apparatus 40 and fixed reference orifice means 50 for the measurement of the pores. Generally, compressed air from the building supply line 56 is passed through a coalescing filter and dryer 58 to a solenoid valve 59. Once the enhanced tube is completely into the cavity measurement section 18 a limit switch (not shown) is activated and the solenoid valve 59 is energized to supply air to the clamping mechanisms 54. The clamping mechanisms 54 load the measuring apparatus 40 into mating engagement with the enhanced tube a clearly shown in FIG. 3.

Once the measuring apparatus 40 is matingly engaged with the surface of the evaporator tube, air is supplied through the pneumatic circuit 62 for the measurement of the pores. Again, compressed air from the building supply line 56 is supplied to the pneumatic circuit 62 through a coalescing filter and dryer 64, a high pressure regulator 66, a solenoid valve 68, and a precision pressure regulator 67. When the pneumatic circuit 62 is activated, the solenoid valve 68 opens and the air flows through the precision pressure regulator 67 and into the supply plenum 65. Air from the supply plenum 65 flows to each of the measuring apparatus 40 and the reference orifice means 50. Generally, one-half of the air pressure from the supply plenum 65 to the measuring apparatus 40 is lost across the flow control valves 72 in the flow paths. The remainder of the air pressure is then lost across the pores of the enhanced tube. Similarly, air from the supply plenum flows to the reference orifice means 50 whereby generally one-half of the air pressure is lost across the flow control valve 73 and the remainder of the air pressure is lost across the fixed reference orifice plate means 50.

Figure 3:
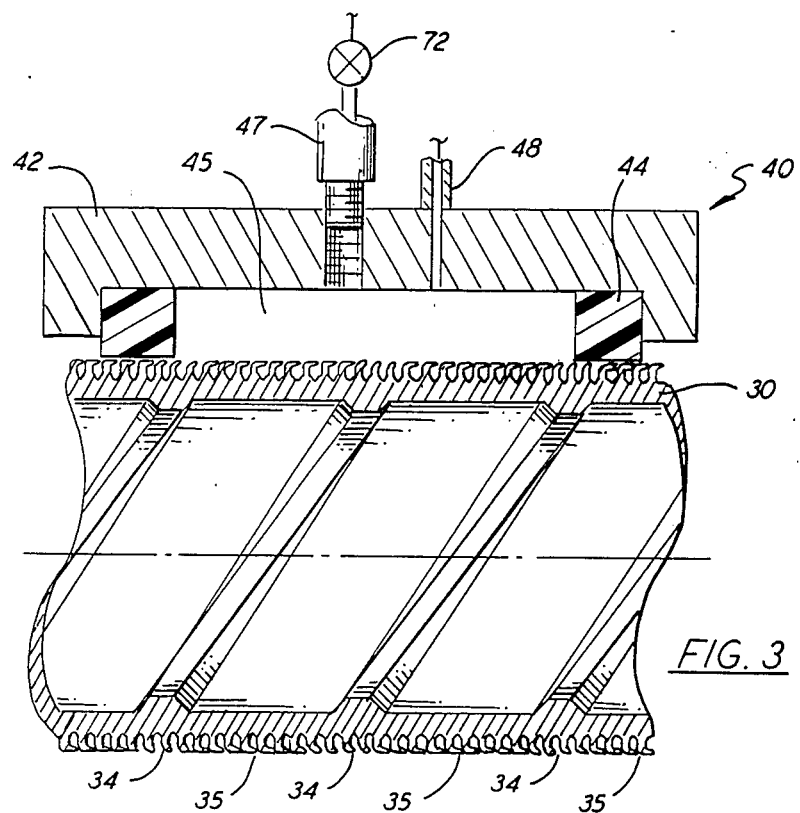
FIG. 3 is a vertical section of a part of an enhanced tube incorporating the pore measuring device in accordance with the present invention.

FIG. 3 shows an enhanced evaporator tube 30 consisting of subsurface channels 35 communicating with the surroundings of the tube through the pores 34. The measuring apparatus 40 comprises a rectangular block 42 and a flexible insert 44 having an arcuate longitudinal channel therein whereby the flexible insert matingly engages with the surface of the enhanced tube 30. Flexible insert 44 acts like a gasket against the surface of the enhanced tube. Thus, when air is blown into chamber 45 through flow control valve 72 and inlet 47, having the flexible insert 44 sealed against the surface of the enhanced tube, the air in chamber 45 enters pores 34 in the surface of the tube within a projected area of the chamber 45 and flows through corresponding subsurface channels 35 and out pores 34 outside the projected area of the chamber to the surroundings.

Figure 4:
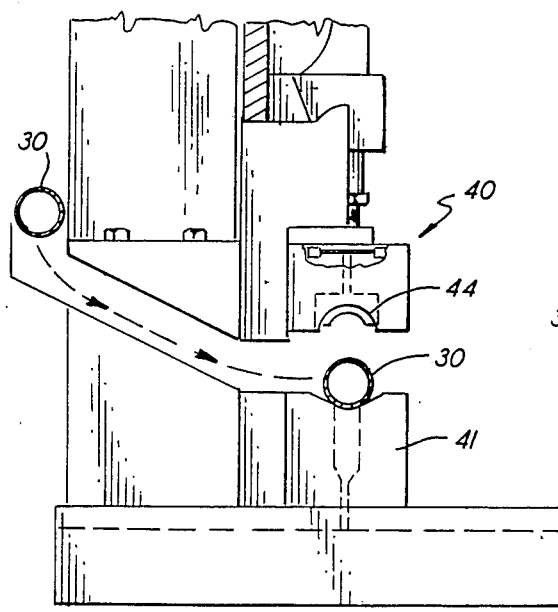
FIG. 4 is a transverse elevational view of the pore measuring device of the present invention.
Figure 5:
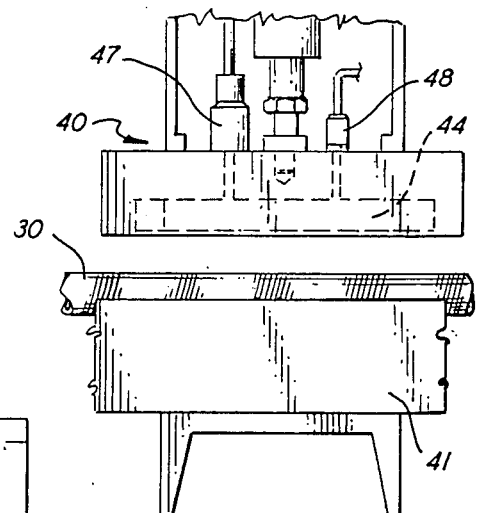
FIG. 5 is a front elevational view of the pore measuring device shown in FIG. 4.

FIGS. 4 and 5 show an enhanced tube 30 supported in a channel support 41 below a pore measuring apparatus 40. The air inlet 47 is supplied with air from flow control valve 72. The air pressure at outlet 48 is then felt at one side of the differential pressure gage 74. With the enhanced tube in the channel support 41, the measuring apparatus 40 is lowered by the clamping mechanisms 54, so that the flexible insert 44 matingly engages with the surface of the tube as shown in FIG. 3. Accordingly, during operation, with constant pressure air flowing through precision regulator 67 a portion of the pressure is lost across flow control valves 72 and 73 in the flow path of the measuring apparatus 40 and fixed reference orifice means 50, respectively. The remainder of the pressure, is lost across the pores of the enhanced tube or the fixed reference orifice means 50. Thus, the differential pressure between the pressure lost across the surface pores and the pressure lost across the fixed reference orifice means, as sensed by differential pressure transducer 74, is a measure of the average pore size on the tube. This average pore size measurement is directly related to the boiling heat transfer coefficient of the tubes. A correlation can thus be established between the pressure drop across the pores of the tube and the expected boiling heat transfer coefficient.

The theory involved in this invention is that the pressure drop across an orifice is a function of the area of the orifice. If an enhanced tube with pores on the surface leading to subsurface channels has compressed air blown through the pores, and simultaneously compressed air is blown through a fixed reference orifice of known area, the difference in the pressure drop across the pores and the fixed reference orifice gives a measure of the average size of the pores on the enhanced tube. A differential pressure is a measure of the pore size and correlates to the expected boiling heat transfer coefficient of the tube.

In operation, an enhanced evaporator tube comprising a continuous subsurface channel with a closed surface having pores spaced along the closed surface, is engaged by a pore size measuring apparatus comprising a generally rectangular block 42 having a passageway therein in which a flexible sealing means having a chamber therein is secured. The chamber has an inlet, through which air from a regulated air source is blown, and an outlet leading to one side of a differential pressure transducer. The other side of the differential pressure transducer is connected to a fixed reference orifice means having a known orifice area which corresponds to the pore area of a desired tube. Accordingly, when the tube has the exact right pore size, the pressure lost across the pores of the tubes is the same as that lost across the fixed reference orifice means, and the pressure drop across flow control valve 72 is the same as the pressure dropped across flow control valve 73. A slight decrease in the pore size of the tube being measured will cause the differential pressure transducer 74 to see a change in the differential pressure. A slight increase in the pore size will cause the transducer to see an opposite change in the differential pressure.

An exemplary apparatus for measuring the pore size of enhanced tubes is shown in FIG. 2. It is preferred that a plurality of measuring apparatus 40 be used along the length of the enhanced tube in order to obtain a better average pore size during the manufacturing process of the enhanced tube. However, one measuring apparatus in conjunction with one fixed reference orifice means is sufficient to obtain the average pore size of the enhanced tube. Before the measuring system can be used, it must be properly calibrated. In this regard, the proper orifice plate for the fixed reference orifice means is selected. The orifice plate is generally a piece of flat stock through which precision holes are drilled whereby the area of the drilled holes is equivalent to the desired area of the pores per unit surface area of the tube. After the proper orifice plate is selected, the output of the precision pressure regulator 67 is adjusted to supply a known pressure to the supply plenum 65 and then the flow control valve 73 is adjusted to drop approximately one-half of the pressure across the flow control valve. Then the flow control valves 72 are adjusted so that the pressure transducer 74 reads zero differential pressure with a test tube or optimum tube having the desired pore size, which correlates to a desired boiling heat transfer coefficient, engaged by the measuring apparatus. If for example the building supply air is 150 psig then pressure regulator 66 will generally reduce this pressure to 75 psig. Thereafter, precision pressure regulator 67 is adjusted to supply 4.0 psig to the supply plenum 65, and the flow control valve 73 is adjusted to drop one-half of the pressure across the valve and the remainder of the pressure across the fixed reference orifice means, while the flow control valve 72 is adjusted to give 0.0 psid at the pressure transducer 74 with a tube having the desired boiling heat transfer coefficient in the apparatus. Once the system is calibrated, enhanced tubes may be produced and the pore size measured in production quantities since the production tube having the exact right pore size will measure 0.0 psid at differential pressure transducer 74.

Of course, the foregoing description of a method and apparatus for measuring the pore size of enhanced tubes is directed to a preferred embodiment, and various modifications and other embodiments will be readily apparent to one of ordinary skill in the art to which the present invention pertains. Therefore, while the present invention has been described in conjunction with a particular embodiment, it is to be understood that various modifications and other embodiments of the present invention may be made without departing from the scope of the invention as described herein and as claimed in the appended claims.

What is claimed is:

1. A pore measuring system for accurately measuring during production the average pore size on the surface of an enhanced evaporator tube having subsurface channels connected by pores on the surface, the average pore size measuring system comprising:
    a fluid pressure source;
    two separate fluid pressure flow path means in fluid flow communication with said fluid pressure source, a first fluid pressure flow path including at least two parallel fluid pressure flow circuit means, a first fluid pressure flow circuit means having an adjustable flow control valve and a movable test housing downstream of said adjustable flow control valve for matingly engaging a portion of the surface of the enhanced evaporator tube, said movable test housing defining a passage for the flow of said fluid pressure source through the pores on the enhanced evaporator tube to the surroundings to reduce the fluid pressure downstream of said first fluid pressure flow path adjustable flow control valve, and a second fluid pressure flow circuit means having a second adjustable flow control valve and a reference orifice downstream of said second adjustable flow control valve, said reference orifice having a predetermined area, a second fluid pressure flow path means including a clamp means for moving said movable test housing by fluid pressure from said fluid pressure source into mating engagement with a portion of the surface of the enhanced evaporator tube; and
    a differential pressure transducer means for measuring the difference in pressure between said at least two parallel fluid pressure flow circuit means whereby one side of said differential pressure transducer means is connected in fluid communication downstream of said adjustable flow control valve and another side of said differential pressure transducer means is connected in fluid communication downstream of said second adjustable flow control valve thereby measuring the difference in pressure drop across the subsurface channels between pores on the enhanced evaporator tube and the pressure across said reference orifice.

2. An enhanced evaporator tube pore size measuring system as set forth in claim 1 wherein said fluid pressure source is a constant air pressure supply.

3. A method for the measurement of the average pore size on the surface of an enhanced evaporator tube having subsurface channels connected by pores on the surface, comprising the steps of:
    supplying a constant fluid pressure simultaneously to two separate fluid pressure flow paths, a first fluid pressure flow path including at least two parallel fluid pressure flow circuit means, a first fluid pressure flow circuit means having a first adjustable flow control valve and a movable test housing downstream of said first adjustable flow control valve for matingly engaging a portion of the surface of the enhanced evaporator tube, and a second fluid pressure flow circuit including a second adjustable flow control valve and a reference orifice downstream of said second adjustable flow control valve, said reference orifice having an orifice area generally equal to the desired area of the pores per unit surface area of a tube, and, a second fluid pressure flow path means including a clamp means for moving said movable test housing by fluid pressure from said fluid pressure source into mating engagement with a portion of the surface of the enhanced evaporator tube;
    energizing said clamp means for placing a tube having the desired area of the pores per unit surface area in mating engagement with said test housing;
    adjusting the first and second adjustable flow control valves until the differential pressure between downstream of said first and second adjustable flow control valves is a selected amount;
    replacing the tube having the desired area of the pores per unit surface area in engagement with said test housing with a tube having the pore size to be measured;
    energizing said clamp means for supplying said fluid pressure from said second fluid pressure flow path to move said movable test housing into mating engagement with said tube to be measured;
    mesuring the differential pressure between downstream of said first and second adjustable flow control valves; and
    determining the average pore size of the surface of the enhanced evaporator tube in engagement with said movable test housing from the difference in said selected amount of differential pressure and said measured differential pressure.

* * * * *